(12) United States Patent
Matusch

(10) Patent No.: US 8,092,419 B2
(45) Date of Patent: *Jan. 10, 2012

(54) DISPOSABLE INJECTOR WITH AT LEAST ONE SUPPORT ROD

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/592,339

(22) Filed: Nov. 23, 2009

(65) Prior Publication Data

US 2010/0076373 A1 Mar. 25, 2010

Related U.S. Application Data

(63) Continuation-in-part of application No. PCT/EP2008/004948, filed on Jun. 19, 2008.

(30) Foreign Application Priority Data

Jul. 6, 2007 (DE) .......................... 10 2007 031 630

(51) Int. Cl.
*A61M 5/30* (2006.01)
(52) U.S. Cl. ........................................... 604/68; 604/72
(58) Field of Classification Search .................. 604/368, 604/90, 311, 68–82
See application file for complete search history.

(56) References Cited

U.S. PATENT DOCUMENTS

| 4,227,528 | A | 10/1980 | Wardlaw |
| 5,681,291 | A | 10/1997 | Galli |
| 6,258,068 | B1 | 7/2001 | Kirchhofer et al. |
| 6,793,646 | B1 * | 9/2004 | Giambattista et al. .......... 604/90 |
| 2005/0137571 | A1 | 6/2005 | Hommann |
| 2006/0189938 | A1 * | 8/2006 | Hommann et al. ........... 604/137 |
| 2006/0264830 | A1 | 11/2006 | Hommann |
| 2008/0146997 | A1 | 6/2008 | Hoffmann |

FOREIGN PATENT DOCUMENTS

| CA | 1295902 C | 2/1992 |
| DE | 38 14023 A1 | 1/1989 |
| DE | 20 2004 016 787 U1 | 2/2005 |
| EP | 1 336 419 A | 8/2003 |
| EP | 1336419 A | 8/2003 |
| WO | WO 0193926 A | 12/2001 |
| WO | WO 2006/088513 A | 8/2006 |
| WO | WO 2006 088513 A | 8/2006 |

* cited by examiner

*Primary Examiner* — Nicholas Lucchesi
*Assistant Examiner* — Leah Stohr
(74) *Attorney, Agent, or Firm* — R. S. Lombard; K. Bach

(57) ABSTRACT

A disposable injector with a housing (10) in which are arranged at least one mechanical spring energy reservoir (50), at least cylinder/piston unit (100) filled with an injection solution, at least one piston-actuating ram, and at least one trigger unit. The spring-loaded piston-actuating ram is supported on the housing via at least one support rod (21), wherein the contact zone located between an individual support rod and the piston-actuating ram represents a wedge gear pairing that forces the respective support rod radially outwards. The support rod or support rods bear on at least one activation element (82) that is mounted on the housing and positioned in a locking position. The activation element can be brought by displacement into a triggering position that releases the piston-actuating ram.

15 Claims, 5 Drawing Sheets

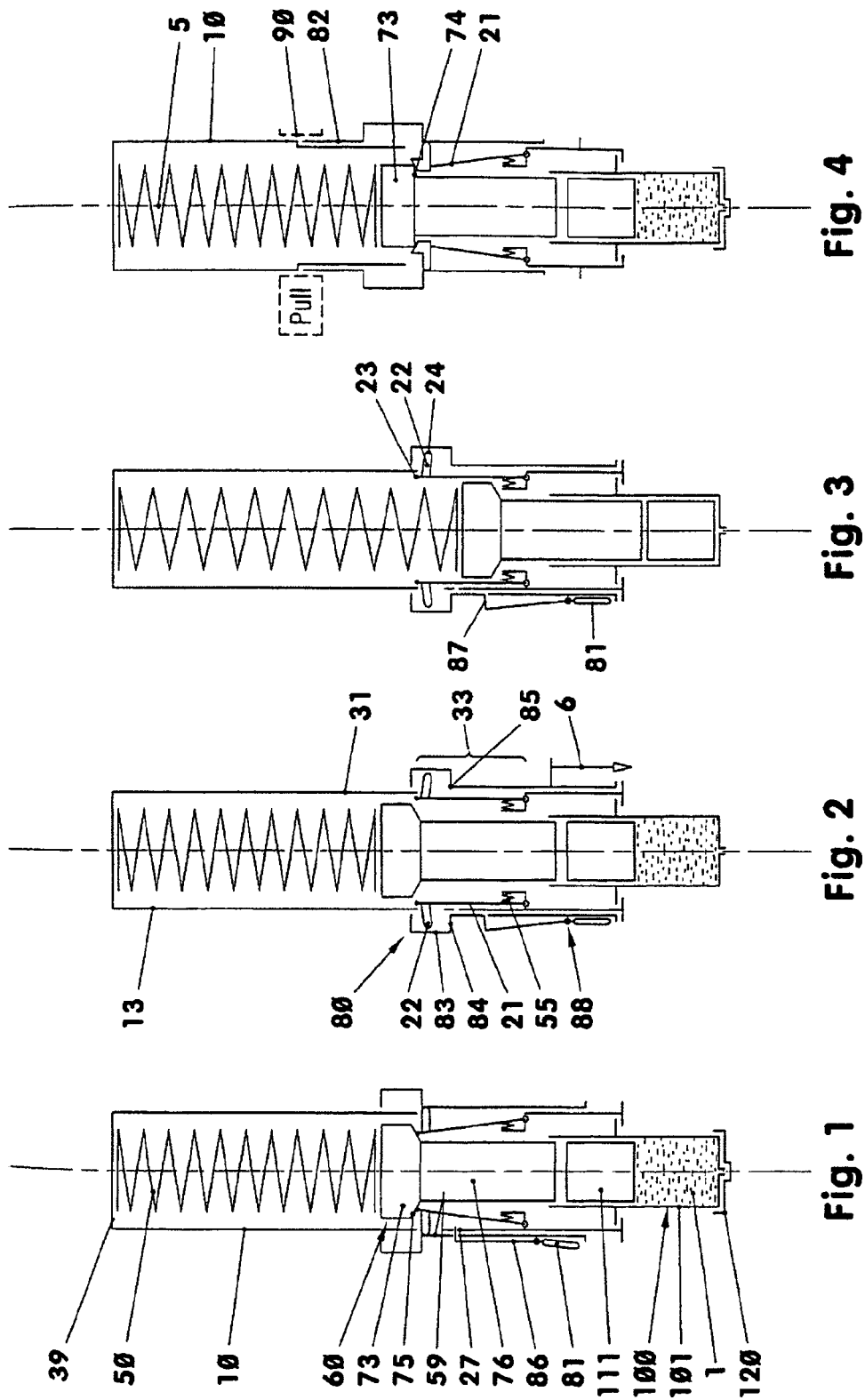

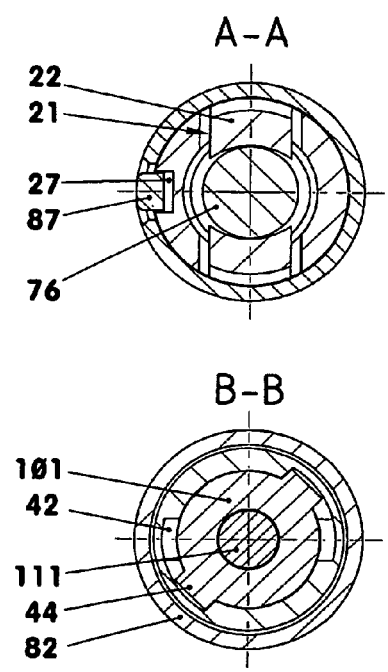
Fig. 6
Fig. 7
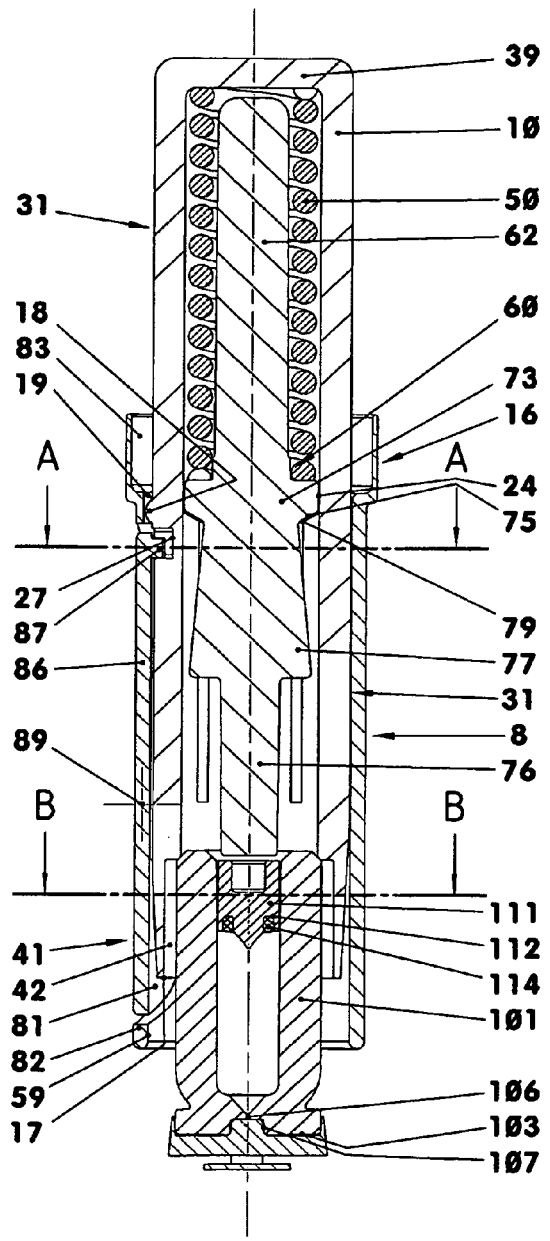
Fig. 5

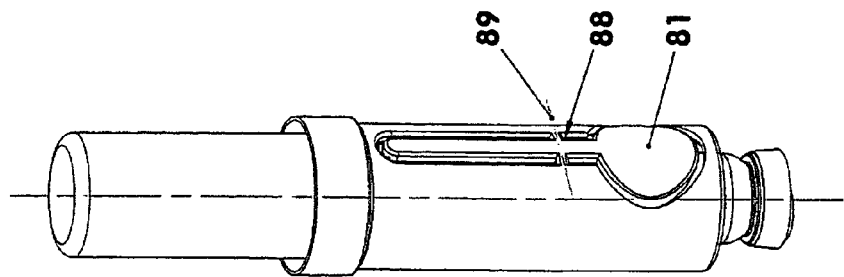
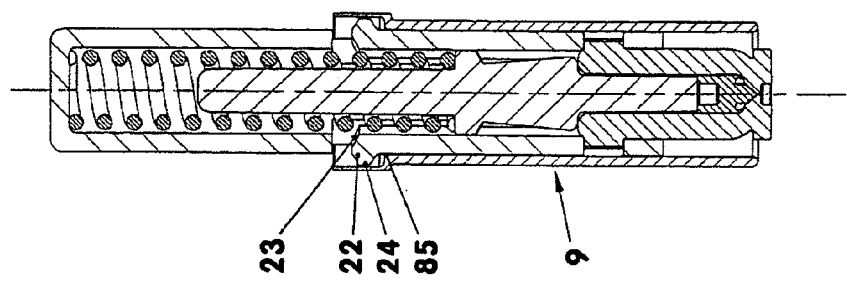
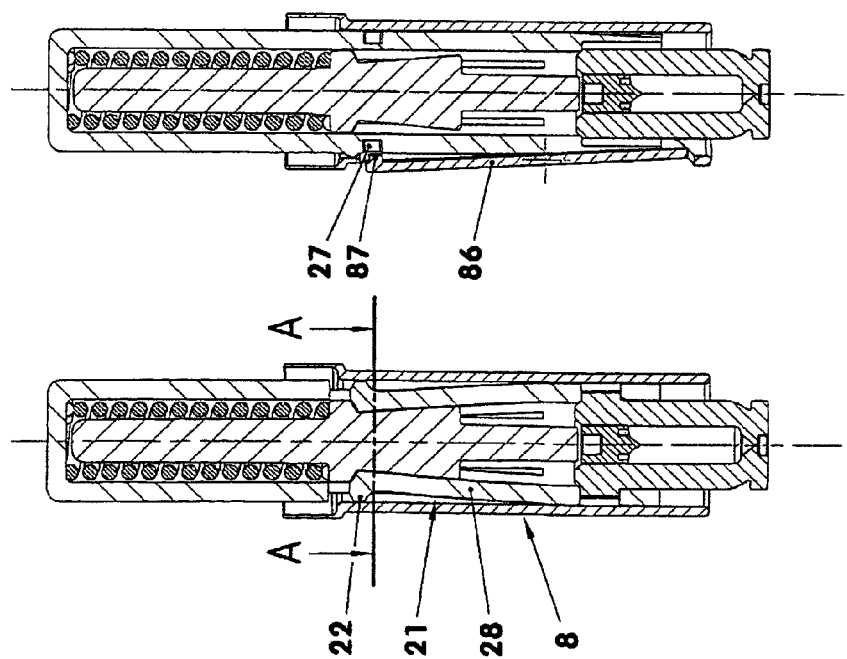

DISPOSABLE INJECTOR WITH AT LEAST ONE SUPPORT ROD

CROSS-REFERENCE TO RELATED APPLICATION

This is a continuation-in-part application of pending international application PCT/EP2008/004948 filed Jun. 19, 2008 and claiming the priority of German Application No. 10 2007 031 630.7 filed Jul. 6, 2007.

BACKGROUND OF THE INVENTION

The invention relates to a disposable injector with a housing, in which or on which—respectively at least in certain areas—at least one mechanical spring-energy storage, at least one cylinder-piston unit which can be filled at least occasionally with active ingredient, at least one piston-actuating plunger and at least one actuating unit are arranged, whereby the spring-energy storage includes at least one pre-stressed spring-loaded element and whereby at least part of the piston-actuating plunger is positioned between the spring-energy storage and the piston of the cylinder-piston unit.

DE 36 44 984 A1 discloses inter alia such an injector which has a spring pre-stressed piston-actuating plunger, whereof the rearward plunger rod has elastic draw hooks at its free end. The draw hooks hold the piston-actuating plunger positively firmly on one edge of the injector housing. For this they have only minimal bearing surface on the housing. To release the injector the draw hooks are pushed away from the edge holding them. As a result, the spring pre-stressed piston-actuating plunger advances to complete injection.

EP 1 336 419 A1 and WO 2005/044344 A1 each describe a needle injector which has a needle guard device and whose piston-actuating plunger is a tension rod or a tension sleeve. The piston-actuating plunger, which is tensioned by a helical compression spring that drives the piston during the injection, is supported on support elements on the housing. The support elements bear on the smallest diameter of the piston-actuating plunger, as a result of which a particularly large surface pressure is obtained in the contact zone.

The object of the present invention is therefore to develop a modular disposable injector which has only a few components for its minimal structural size and guarantees secure mounting and function with easy handling.

SUMMARY OF THE INVENTION

The invention relates to a disposable injector with a housing (10) in which are arranged at least one mechanical spring energy reservoir (50), at least cylinder/piston unit (100) filled with an injection solution, at least one piston-actuating ram, and at least one trigger unit. The spring-loaded piston-actuating ram is supported on the housing via at least one support rod (21), wherein the contact zone located between an individual support rod and the piston-actuating ram represents a wedge gear pairing that forces the respective support rod radially outwards. The support rod or support rods bear on at least one actuating element (82) that is mounted on the housing and positioned in a locking position. The actuating element can be brought by displacement into a triggering position that releases the piston-actuating ram.

For this purpose, the spring-loaded piston-actuating plunger is supported on the housing via at least one support rod, and the contact zone located between an individual support rod and the piston-actuating plunger represents a wedge mechanism pairing that forces the respective support rod radially outwards. The support rods bear on, and force radially outwards, at least one actuating element that is mounted on the housing and located in a locked position. The actuating element, as part of an actuating unit, can be brought by displacement into an actuating position that releases the piston-actuating plunger, there being no supporting action in the actuating position.

The invention provides for example a needle-free disposable injector, whereof the piston-actuating plunger is released with a triggering procedure of the disposable injector. For this purpose, for pre-stressing and holding the spring-energy storage the piston-actuating plunger is held positively by at least one support rod arranged on the housing or integrated in the housing. The support rod or the support rods is/are held by an actuating element until the disposable injector is used in its locked position. To trigger the injector the support rod or the support rods is/are released so that the piston-actuating plunger can move under the effect of the spring-energy storage at least approximately parallel to the centre line of the disposable injector.

BRIEF DESCRIPTION OF THE DRAWINGS

Further details of the invention will become clear from the following schematically illustrated embodiments, in which:

FIG. 1 illustrates a disposable injector with two support rods and lever retention;

FIG. 2 as for FIG. 1, however unlocked and actuated;

FIG. 3 as for FIG. 2, however following drug ejection;

FIG. 4 illustrates a disposable injector with two support rods and banderole retention;

FIG. 5 illustrates a disposable injector with two compression bars deformed in locked position and actuating lever;

FIG. 6 is a cross section A-A of FIGS. 5 and 8;

FIG. 7 is a cross section B-B of FIG. 5;

FIG. 8 as for FIG. 5, however, turned 90°;

FIG. 9 as for FIG. 5, however unlocked;

FIG. 10 as for FIG. 8, however unlocked and actuated;

FIG. 11 is a diametrical view of FIG. 5;

DETAILED DESCRIPTION OF THE PARTICULAR EMBODIMENTS

Figure 12:
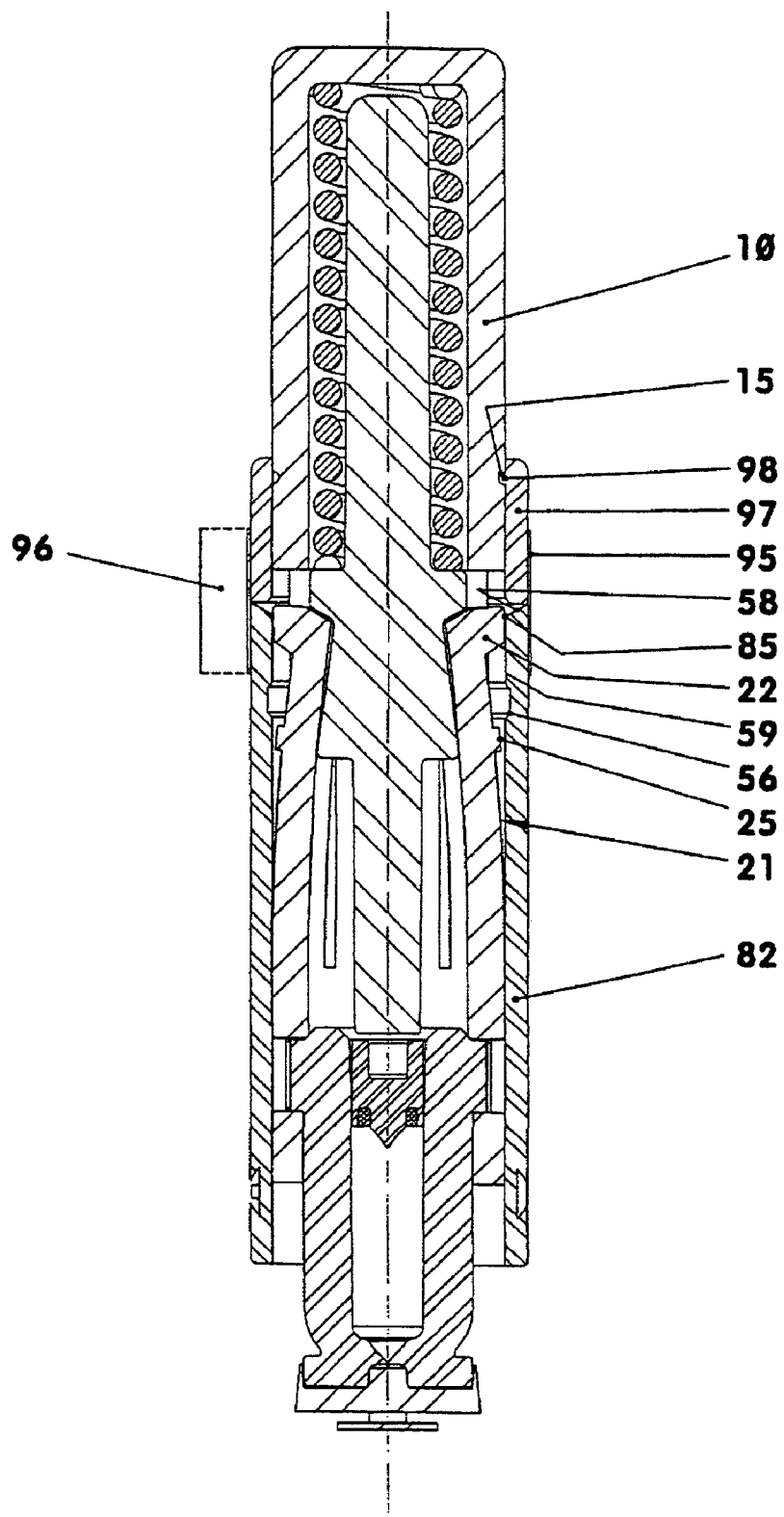
FIG. 12 illustrates a disposable injector with two compression bars formed in the locked position and banderole retention.
Figure 16:
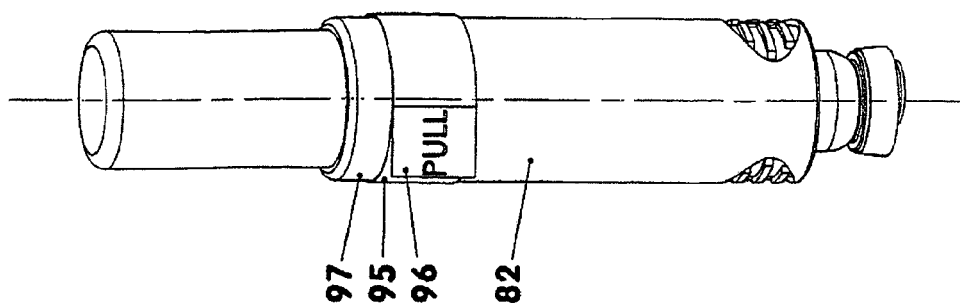
FIG. 16 is a diametrical view of FIG. 15.
Figure 15:
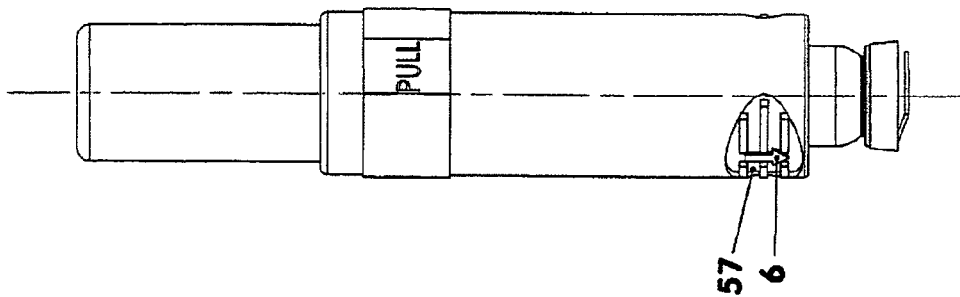
FIG. 15 is a side view of the injector.

FIGS. 1 to 3 show a simplified main sketch of a disposable injector type with permanently loaded spring-energy storage in three different release states. The illustrated disposable injector comprises a housing (10), a cylinder-piston unit (100) pre-filled with e.g. an injection solution, a piston-actuating plunger (60) and a screw compression spring (50) as spring-energy storage. Also, an actuating element (82) and a retaining element (86, 90) are arranged on the housing (10). The cylinder-piston unit (100) is sealed from the front by a protective cap (120).

The housing (10) is a pot-shaped hollow body, open at the bottom and with an elevated floor (39). The housing (10) has e.g. two opposite window-like openings (33) in the middle region, the shell region (31). Articulated respectively at the lower edge of an opening (33) is in each case a support rod (21), as in FIG. 2, right side of the injector. On the left-hand side of the housing (10), the opening (33) is depicted smaller in the schematic diagram so as to be able to show the securing actuating lever (86, 87). The actuating lever (86, 87) sits in the housing (10) generally offset by e.g. 90 degrees, cf. FIG. 6.

The support rods (21) are placed here only by way of example in drag-hinges and supported by spring-loaded elements (55) on the housing (10). The spring-loaded elements (55) press the support rods (21) at least approximately radially outwards against the actuating element (82), as in FIG. 1, where they rest on the actuating element (82) via cams (22). If the support rods (21) are formed on the housing (10), as in FIGS. 5 and 12, they spring outwards as elastic flexional beams (28).

Both pressure-stressed support rods (21) hold the piston-actuating plunger (60) on its plunger disc (73) in its pre-stressed position, as in FIG. 1. For this purpose, the support rods (21) are supported on the frustoconical or spherically curved lower front end face (74) of the plunger disc (73) by their support surfaces (23). The size of the respective contact surface between a support surface (23) and the corresponding surface of the front end face (74) is in the region of 2 to 20 mm$^2$.

On the side averted from the centre line (5) each support rod (21) has a contact surface (24) on its cam (22).

Located in the lower region of the housing (10) are holders for fastening the cylinder-piston unit (100).

In this embodiment the cylinder-piston unit (100) comprises a cylinder (101) filled with an injection solution (1), in which a piston (111) sits in the rear position. Above the piston (111) in the housing (10), the piston-actuating plunger (60) is e.g. arranged such that although it does not touch the piston, it is guided sideways by its lower end in the upper region of the cylinder (101).

As shown in FIG. 4 the lower half of the housing (10) is enclosed by the sleeve-like actuating element (82). The actuating element (82) is mounted to move lengthways on the radial outer surface (13) of the housing (10). It has a circumferential widened region (83) in the upper region at the level of the cams (22). There can also be partially widened regions or uncovered openings instead of this widened region (83) in the case of a non-rotating symmetrical actuating element (82) per support rod (21).

With respect to the housing (10) the widened region (83) is positioned and dimensioned so precisely that it can take up the outwards-thrust compression bars (21) with their cams (22) retreating during the triggering procedure. The inner contour of the widened region (83) is e.g. a channel with a return flank (84), which here represents a plane normal to the centre line (5) of the injector. The transition between for example the cylindrical inner walls of the actuating element (82) and the return flank (84) is configured e.g. as a sharp edge (85). According to FIG. 1 the cams (22) with their outer contact surfaces (24) lie protectively on the inner walls (59) of the actuating element (82).

A securing actuating lever (86) is fastened or formed integrally on the actuating element (82). The actuating lever (86) has a pushbutton-like operating element (81) at its lower end, a latching lug (87) at its upper end, and, between the parts (81) and (87), it has a pivot joint (88) on which the actuating lever (86) is mounted. According to FIG. 1, the latching lug (87) projects with a locking action into a recess (27) of the housing (10).

The piston-actuating plunger (60) arranged in the housing (10) is divided here into two regions. The lower region is the piston slide (76). Its diameter is somewhat smaller than the inner diameter of the cylinder (101) of the cylinder-piston unit (100). The lower front end of the piston slide (76) acts directly on the piston (111).

The upper region, the plunger disc (73), is a flat disc, cylindrical at least in certain areas, whereof the outer diameter is a few tenths of a millimeter smaller than the inner diameter of the housing (10) in the shell region (31). The lower front face (74) has a collar surface (75) arranged around the piston slide (76). It has the shape of a frustoconical surface, whereof the apex angle is from about 100 degrees to about 130 degrees, preferably 120 degrees of angle. The notional tip of the frustoconical surface lies on the centre line (5) in the region of the piston slide (76).

The piston slide (76) can of course also be designed as a separate component, separate from the plunger disc (73). For this purpose it is located on the inner walls of the housing (10).

The screw compression spring (50) sits pre-stressed between the plunger disc (73) and the superjacent floor (39) of the housing (10). The resilient force is transferred via the plunger disc (73) to the support rods (21). Due to the inclination of the collar surface (75) the compression bars (21) are thrust radially outwards in the manner of a bevel gear. The release sleeve (82) steadily supports this radial force.

After the protective cap (120) of the cylinder-piston unit (100) is removed the disposable injector is positioned on the injection site to actuate the disposable injector. The disposable injector is held between the thumb and the other fingers of the hand holding the injector. The thumb bears on the operating element (81). If the operating element (81) or parts of the actuating lever are additionally secured, for example, by an adhesive label or the like, then these have to be removed before the following operating step.

When the operating element (81) is pressed, the latching lug (87) of the actuating lever (86) pivots out of the housing recess (27). The secure catch between the housing (10) and the sleeve-shaped actuating element (82) is cancelled. The actuating element (82) can now be pushed in the direction of the cylinder-piston unit (100). During this procedure the actuating element (82) slides on the outer walls (13) of the housing (10) downwards and linearly, therefore in the direction of the injection site. The contact surfaces (24) of the compression bars (21) skid over the edge (85) and spring radially outwards in release into the widened region (83) under the force of the spring-loaded element (50). The piston-actuating plunger (60) shoots unhindered downwards, as in FIG. 3. The cylinder (100) is emptied.

A helical movement can also be provided instead of a linear sliding motion of the actuating element (82) on the housing (10). In this case the actuating element (82) and the housing (10) are guided towards one another e.g. via a slide block and a motion link. If required, triggering can also be realized by a pure pivoting movement between the housing (10) and the actuating element (82). The pivot axis here would be the centre line (5).

FIG. 4 shows a variant that does not require an actuating lever (86). Instead, the actuating element (82) is extended in the upward direction. The upper, extended end of the actuating element (82) is secured on the housing (10) with a banderole (90). The tear-off or tear-open banderole (90) temporarily binds the parts (10) and (82). To prime the injector, the banderole (90) is pulled off or torn open such that the binding connection between the housing (10) and the actuating element (82) is cancelled.

With this variant the collar surface (75) of the plunger disc (73) is designed flat. The collar surface (75) is oriented normally to the centre line (5). By way of a rounded edge it contacts the upper front ends of the support rods (21). These front ends are curved in a wedge, truncated or spherical shape. The curving is respectively oriented such that a force acting radially outwards is exerted on the support rods (21), as for the variant in FIGS. 1 to 3.

FIGS. 5 to 11 show an embodiment of the principle described in FIGS. 1 to 3. Here the load-bearing component is a one-piece housing (10). It is made from e.g. a fibreglass-reinforced polyamide by injection moulding. The housing (10) has an extensively tubular shape and is divided into two functional areas, comprising both the upper shell region (31) and the lower fixing region (41).

The substantially tubular shell region (31) is sealed at the top by an e.g. level floor (39). Located in the lower half of the shell region (31) are two opposite formed-on drawbars (21), as in FIGS. 8 and 10. The forming-on site for the drawbars (21) is just above the fixing region (41). For forming the respective support rod (21) there is located in the shell section (31) a narrow, at least approximately U-shaped gap, surrounding the individual support rod to the sides and at the top. Over ca. 80% of its length the support rod (21) has the wall thickness and curve of the walls of the housing (10). This region inter alia also functions as a sprung-elastic flexional beam (28) and has a sickle-shaped cross-section.

If required, part of this flexional beam (28) can also be equipped with a rectangular cross section to reduce bending stresses occurring from use in the flexional beam edge region. In FIG. 10 the support rod (21) is shown in the undeformed state.

The upper free end of the individual support rod (21), as in FIGS. 8 and 10, is here formed by the radially outwards projecting cam (22), which has at least one support surface (23) and one contact surface (24). According to FIG. 8 the plunger disc (73) of the stressed disposable injector lies on the support surface (23) by its collar surface (75). The support surface (23), here fulfilling the function of a wedged face, has the form of a frustoconical surface with an apex angle of 120 degree of angle.

At least in the contact region the support rods (21) or the collar surface (75) may have ceramic armouring. In the embodiment in FIG. 5 the collar surface (75) is reinforced by an e.g. stuck-on, centrally divided, frustoconical surface-shaped washer (79).

The contact surface (24) of the cam (22) of the undeformed support rod (21) is part of a cylindrical shell, whereof the diameter is e.g. 3 to 4 millimeters larger than the outer diameter of the housing (10). When the disposable injector is stressed the contact surface (24) contacts the inner walls (59) of the sleeve-like actuating element (82). If required, to minimize the surface pressure the contact surface (24) has a curve, which corresponds to the inner walls (59).

According to FIG. 5, the housing (10) has, approximately at the centre (cf. section line A-A), a recess (27) in which the latching lug (87) of the actuating lever (86) engages. FIG. 6 shows the engagement in cross section. The two support rods (21) with the cams (22) can also be seen in this cross section.

A web (18) for securing against rotation is located above the recess (27). It engages in a corresponding groove (19) of the actuating element (82) in order to secure against rotation.

Situated under the shell section (31) is the fixing region (41) for taking up the incorporable cylinder-piston unit (100). The fixing region (41) is part of a bayonet closure. For this purpose, two or more angular channels (42) are arranged on its inner wall, cf. FIG. 7. The channels (42) lead vertically upwards from the lower front face (17) of the housing and, after a length of a few millimeters, each merge into a short horizontal channel portion. If appropriate, the transverse channel areas form a radially continuous recess.

The cylinder (101) is fitted and fixed in the fixing region (41) via, for example, two or more bayonet studs (44), cf. FIG. 7. If appropriate, one or more catch elements, which prevent release of the bayonet closure, in other words removal of the cylinder (101), are located in the horizontal channel portion or on at least some of the bayonet studs (44).

The cylinder (101) is e.g. a thick-walled pot. In the for example cylindrical bore of the cylinder (101) sits the rod-less piston (111). On its at least approximately conical front end the piston (111) has an axial annular groove (112) for receiving a sealing ring (114) or a permanently elastic sealing mass. Set into the rear front end of the piston (111) where required is an e.g. cylindrical metal plate.

Located in the centre of the bore of the cylinder (101), whereof the cylindrical floor matches the contour of the front piston front face at least approximately, is a short cylindrical, nozzle-like bore (106). Its diameter is ca. 0.1 to 0.5 millimeters. This bore (106) is one to five times as long as its diameter. It ends in a cylindrical recess (107) of the floor-side outer front end (103) of the cylinder (101).

In the fixing region (41), the outer wall of the housing (10) has a frustoconical shape. The wall thickness decreases by ca. 20% towards the front face (17), such that the pushbutton (81) can retreat when operated.

Arranged between the piston (111) and the floor (39) is the spring-energy storage (50) or respectively the drive unit of the disposable injector. The spring-energy storage (50) is a screw compression spring, arranged on the piston-actuating plunger (60) with the plunger disc (73). The resilience-stressed piston-actuating plunger (60) is supported on the support rods (21) of the housing (10) by means of the plunger disc (73).

Above the plunger disc (73) the piston-actuating plunger (60) has a pilot pin (62) which guides the screw compression spring (50). Located centrally under the plunger disc (73) in the extension of the pilot pin (62) is the piston slide (76), which acts on the piston (111) when the disposable injector is actuated. The upper area of the piston slide (76) has a conical widening (77) whose length is half the length of the piston slide (76). The diameter of the widening (77) increases in the direction away from the plunger disc (73). The support rods (21) bear on the widening (77) when the injector is tensioned. This counteracts any buckling of the permanently loaded support rods (21).

The actuating element (82) partially enclosing the housing (10) and the cylinder-piston unit (100) is here likewise a release sleeve. The essentially cylindrical release sleeve (82), e.g. made of ABS, has at its upper end an annular radial widened region (83), which takes up the cams (22) of the support rods (21) when the disposable injector has been triggered, as in FIG. 10.

The actuating lever (86) is integrated in the at least approximately cylindrical area lying underneath, cf. FIG. 11. Said actuating lever (86) is connected to the actuating sleeve (82) via a pivot joint (88). Together with the operating element (81), the actuating lever (86) forms a rocker, which has its pivot axis (89) in the area of the pivot joint (88). When the actuating lever (86) is pressed against the housing (10) by depression of the operating element (81), the latching lug (87) at the other end of the actuating lever (86) disengages from and frees the recess (27), cf. FIG. 9.

FIG. 9 shows the disposable injector with the actuating lever triggered, i.e. released. In FIG. 10, the injector is shown with the actuating element (82) pushed down.

When the actuating sleeve (82) is pushed down, the cams (22), cf. FIG. 10, slip outwards over the edge (85) into the widened region (83). The support rods (21) bend elastically outwards into their actual starting position. The support rods (21), now no longer deformed, free the piston-actuating plunger (60), such that the piston (111) is pushed back into the cylinder (101) under the action of the spring element (50).

FIGS. 12 to 16 illustrate a support rod injector without actuating lever (86). Instead of the actuating lever, a banderole (95) is used as the original fastener and securing element, as is already known in part from FIG. 4. For this purpose, a retaining ring (97) sits above the sleeve-shaped actuating element (82) guided longitudinally on the housing (10). The tubular retaining ring (97) mounted on the housing (10) has a latching cam (98), which engages in a retaining groove (15) of the housing (10). The retaining ring (97) is fixed axially on the housing (10) via the latching cam (98). If appropriate, instead of the latching cam (98), a ring of cams or even a peripheral latching web is used on the retaining ring (97).

The retaining ring (97) has, for example, a plane lower end face on which, according to FIG. 12, the actuating element (82) adjoins directly with its front end (58). The retaining ring (97) and the actuating element (82) have the same external diameter in this area.

The front end (58) is here a frustoconical surface whose seat on the centre line (5) lies below the retaining ring (97). The cone angle is 120 degrees, for example. The contact line between the front end (58) and the inner wall (59) forms the edge (85) via which the cams (22) slip when the injector is actuated.

Figure 14:
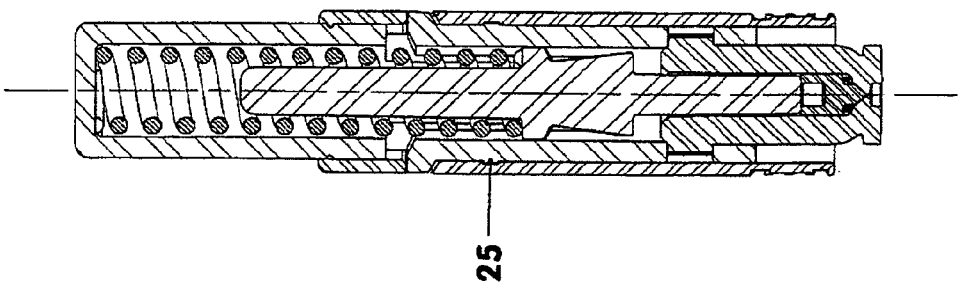
FIG. 14 as for FIG. 13, however actuated.

According to FIG. 14, the cams (22) have an outward radial extent that is smaller than the wall thickness of the actuating element (82) there. Consequently, upon actuation, the cams (22) cannot protrude beyond the outer wall of the actuating element (82).

The retaining ring (97) and the actuating element (82) are bonded to each other via a banderole (95). The banderole (95) is, for example, a strip of paper or film coated on one side with an adhesive. The film strip extends, for example, in one loop around the unit composed of retaining ring (97) and actuating element (82). The upper half of the film strip adheres to the retaining ring (97), and the lower half adheres to the actuating element (82). In the illustrative embodiment, the film strip is ca. 2 to 3 centimeters longer than the circumference of the retaining ring (97). A protruding area that remains when the parts (82, 97) have been fixed together forms a tear-off tab (96). The two to three centimeters long tear-off tab (96) is not coated with adhesive on both sides. When the banderole (95) is completely unwound from the retaining ring (97) and actuating element (82) with the aid of the tear-off tab (96), with release of the adhesive connection, the actuating element (82) can be moved downwards on the housing (10) from the retaining ring (97).

A few millimeters below its upper end face, the actuating element (82) has, for example, a circumferential retaining groove (56) in its inner wall (59). Upon actuation of the injector, special retaining webs (25) of the support rods (21) engage in the retaining groove (56), cf. also FIG. 14. This locking arrangement ensures that the disposable injector cannot be dismantled into its individual parts after use.

In its lower area, the actuating element (82) has, on its outer wall, two flutings (57) with elliptical edges. The flutings or structures are positioned on the outer wall at an angle of 180 degrees. A downward pointing directional arrow (6) is integrated in the fluting (57).

In this variant embodiment, with the exception of the spring-loaded element (50), all components are arranged rotationally symmetrically and/or mirror-symmetrically to a plane laid on the centre line (5), which simplifies assembly.

Figure 13:
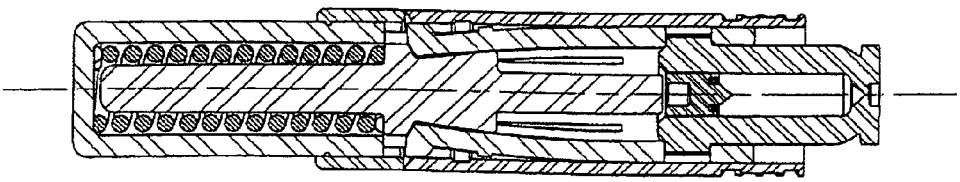
FIG. 13 as for FIG. 12, however unlocked by removal of the banderole.

To operate the injector, the protective cap (120) on the cylinder-piston unit (100) is removed, and the banderole (95) is torn off transverse to the lengthways direction (5) of the injector, e.g. tangentially, cf. FIG. 13, to prime it. After being placed on the injection site, the sleeve-shaped actuating element (82) is pushed downwards. The support rods (21) spring outwards and free the spring-loaded plunger disc (73), cf. FIG. 14. The injection procedure is completed with the dispensing of the medicament via the cylinder-piston unit (100).

With injectors, in which the piston-actuating plunger (60) is guided straightly in the housing (10)—at least in certain areas—with minimal clearance and the piston-actuating plunger (60) has adequate bending strength, only a single support rod (21) can be used instead of two or more support rods (21).

In the variants illustrated in the figures the individual contact zone between the support rod (21) and the plunger disc (73) is designed as surfaces (23) and (74, 75), which glide on each other on contact. In a particular configuration in each surface (23) of the individual support rods (21) a roller can be mounted, which rolls away as a roller bearing, therefore almost frictionless, when the injector is actuated on the surface (74, 75) of the plunger disc.

With the exception of the spring-loaded element (50), where required a piston plate and for example the available bearing roller of the support rods (21), all parts of the previously described disposable injectors are made of plastics or plastic- or rubber-like materials.

LIST OF REFERENCE NUMBERS 1 injection solution; drug
5 centre line of the injector, lengthways direction
6 actuation direction of movement of (82), downwards movement directional arrow
8 locked position
9 actuating position, triggering position
10 housing, one-piece
13 outer surface, cylindrical
15 retaining groove
16 actuating region, upper
17 lower housing front face
18 web for securing against rotation
19 groove in (82)
21 support rods, compression rods
22 cams
23 support surface
24 contact surface
25 retaining webs
27 recess for (87)
28 flexional beams
31 shell region
33 openings
39 floor
41 fixing region for the cylinder-piston unit
42 channels, angular
44 bayonet stud
50 spring-loaded element, screw compression spring, spring-energy storage
55 spring-loaded elements on (21)
56 retaining groove of (82)
57 fluting of (82)
58 front end of (82)
59 inner walls of (82)
60 piston-actuating plunger
62 pilot pin
73 plunger disc 74 front face, lower; front face end
75 collar surface, front face end
76 piston slide
77 cone widening
79 washer
80 actuating unit
81 operating element, pushbutton
82 actuating element
83 widened region
84 return flank
85 edge, sharp-edged
86 actuating lever, retaining element
87 latching lug
88 pivot joint
89 pivot axis
90 original fastener, banderole, retaining element
95 original fastener, banderole, retaining element
96 tear-off tab
97 retaining ring
98 latching cam
100 cylinder-piston unit
101 cylinder
103 front end
106 bore, nozzle
107 recess in the front end
111 piston
112 annular groove
114 sealing ring, seal
120 protective cap, adhesive seal

What is claimed is:

1. A disposable injector comprising:
a housing (10), in which or on which respectively at least in certain areas
at least one mechanical spring-energy storage (50), at least one cylinder-piston unit (100) which can be filled at least occasionally with active ingredient, at least one piston-actuating plunger (60) and at least one actuating unit (80) are arranged,
at least one piston-actuating plunger (60) is positioned between the spring-energy storage (50) and a piston (111) of the cylinder-piston unit (100),
at least one spring-energy storage (50) includes at least one pre-stressed spring-loaded element,
the at least one spring-loaded piston-actuating plunger (60) has a plunger disc (73) for supporting the spring-energy storage (50)
the at least one spring-loaded piston-actuating plunger (60) on the plunger disc (73) is supported on the housing (10) via at least one support rod (21),
the at least one support rod (21) is formed respectively on the housing (10) being affixed at only one end thereof and the at least one support rod (21) being an elastic flexional beam (28), the at least one support rod (21) includes a cam (22) at the free end of the rod (21),
each of the at least one individual support rods (21) forms a wedge gear combination with the plunger disc (73) at a contact zone, the wedge gear combination operatively exerts force on the respective support rod (21) in a radially outward direction,
the piston-actuating plunger (60) has on its front end averted from the spring-loaded element (50) at least in certain areas flat wedged faces or in certain areas single frustoconical faces (74, 75),
the actuating unit (80) includes at least one actuating element (82) with the at least one actuating element (82) mounted on the housing (10), the at least one support rod (21) in operational arrangement with the at least one actuating element (82), in a locked engagement position (8) the at least one support rod (21) bears on, and forces radially outwards the at least one actuating element (82), the actuating element (82) is a slide sleeve mounted slidably on the outside of the housing (10), the actuating unit (80) further includes a securing actuating lever (86) fastened to or formed integrally with the actuating element (82) or the actuating unit (80) further includes a retaining ring (97) mounted in operative position with the housing (10) proximate the slide sleeve actuating element (82),
whereby the actuating element (82), as part of the at least one actuating unit (80), can be brought by displacement into an actuating position (9) that releases the piston-actuating plunger (60) and has no supporting action.

2. The disposable injector according to claim 1, wherein together with every single support rod (21) the piston-actuating plunger (60) forms a spline gear, in which an axial resilient force direction is deflected in a radial support force direction.

3. The disposable injector according to claim 1, wherein the piston-actuating plunger (60) has, in the upper area of the piston slide (76), a conical widening (77) that secures the support rods (21) against buckling in the locked position (8).

4. The disposable injector according to claim 1, wherein each cam (22) of the at least one support rod (21) has at its free end a flat, truncated conical or spherical support surface (23).

5. The disposable injector according to claim 1, wherein the slide sleeve actuating element (82) has a circumferential widened region (83) in the upper region thereof at the level of the cam (22) of the at least one support rod (21) in the locked engagement position (8).

6. The disposable injector according to claim 5, wherein the widened region (83) of the slide sleeve actuating element (82) in operative position upon triggering of the injector is sized to receive cam (22) of the at least one support rod (21) upon cam (22) retreating during the triggering of the injector.

7. The disposable injector according to claim 1, wherein the actuating lever (86) includes a pushbutton-like operating element (81) at the lower end thereof and a latching lug (87) at the upper end thereof and between the pushbutton-like operating element (81) and the latching lug (87), the actuating lever (86) includes a pivot joint (88).

8. The disposable injector according to claim 7, wherein the housing (10) has a recess (27) therein, the latching lug (87) projects in operational arrangement into the recess (27) of the housing (10) in the locked engagement position (8).

9. The disposable injector according to claim 1, wherein the retaining ring (97) has a latching cam (98), the housing (10) has a retaining groove (15), the cam (98) engages the groove (15).

10. The disposable injector according to claim 9, wherein the ring (97) and the activating element (82) have the same external diameter in the area proximate each other.

11. The disposable injector according to claim 10, wherein a front end (58) of the actuating element (82) has a frustoconical surface having a seat lying below the retaining ring (97).

12. The disposable injector according to claim 11, wherein the front end (58) of the actuating element (82) forms with the inner wall (59) of the actuating element (82) an edge (85) via which the cam (22) of the at least one support rod (21) slips when the injector is triggered.

13. The disposable injector according to claim 12, wherein the outward radial extent of the cam (22) of the at least one support rod (21) is smaller than the wall thickness of the actuating element (82).

14. The disposable injector according to claim 10, comprising a tear-off banderole (95) in releasable binding relationship with the actuating element (82) and the housing (10) thereby forming actuating unit (80).

15. The disposable injector according to claim 14, wherein tear-off banderole (95) includes a tear-off tab (96).

* * * * *